United States Patent
Gundlapalli et al.

(10) Patent No.: US 10,645,927 B2
(45) Date of Patent: May 12, 2020

(54) ANTIMICROBIAL WIPE

(71) Applicant: Carefusion 2200, Inc., San Diego, CA (US)

(72) Inventors: Ramarao V. Gundlapalli, South Barrington, IL (US); Hong Shen, Hoffman Estates, IL (US); Kenneth Bruce Thurmond, II, Deer Park, IL (US); Christopher Varga, Laguna Hills, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 16/213,875

(22) Filed: Dec. 7, 2018

(65) Prior Publication Data

US 2019/0104735 A1    Apr. 11, 2019

Related U.S. Application Data

(63) Continuation of application No. 14/985,042, filed on Dec. 30, 2015, now Pat. No. 10,264,788.

(51) Int. Cl.
| | |
|---|---|
| *A01N 43/40* | (2006.01) |
| *A01N 25/34* | (2006.01) |
| *A47L 13/17* | (2006.01) |
| *A61K 8/49* | (2006.01) |
| *A61K 8/02* | (2006.01) |
| *A61Q 17/00* | (2006.01) |
| *C11D 17/04* | (2006.01) |

(52) U.S. Cl.
CPC ............ *A01N 43/40* (2013.01); *A01N 25/34* (2013.01); *A47L 13/17* (2013.01); *A61K 8/0208* (2013.01); *A61K 8/4926* (2013.01); *A61Q 17/005* (2013.01); *C11D 17/049* (2013.01)

(58) Field of Classification Search
None
See application file for complete search history.

(56) References Cited

U.S. PATENT DOCUMENTS

| | | | |
|---|---|---|---|
| 3,967,756 A | 7/1976 | Barish | |
| 4,998,984 A | 3/1991 | McClendon | |
| 6,358,516 B1 * | 3/2002 | Harod | A61K 8/0208 424/401 |
| 6,649,584 B2 | 11/2003 | Wisniewski et al. | |
| 6,737,068 B2 | 5/2004 | Durden | |
| 7,427,574 B2 | 9/2008 | Allen | |
| 2003/0003831 A1 | 1/2003 | Childs et al. | |
| 2006/0079143 A1 | 4/2006 | Phan et al. | |
| 2007/0042666 A1 | 2/2007 | Allen | |
| 2010/0158964 A1 | 6/2010 | Cunningham et al. | |
| 2010/0326418 A1 | 12/2010 | Sesock et al. | |
| 2012/0070510 A1 * | 3/2012 | Krug | A01N 31/02 424/605 |
| 2014/0194803 A1 * | 7/2014 | Parks | A61K 38/2053 602/48 |
| 2015/0190536 A1 | 7/2015 | Degala et al. | |

FOREIGN PATENT DOCUMENTS

| | | | |
|---|---|---|---|
| EP | 1 059 378 A1 | 12/2000 | |
| EP | 2443925 A1 | 4/2012 | |
| WO | 2 443 924 A1 | 4/2012 | |
| WO | WO-2015091692 A1 * | 6/2015 | ........... A61K 31/444 |
| WO | WO 2015/145100 A1 | 10/2015 | |

OTHER PUBLICATIONS

Koopman, D.C., "Comparison of Dow Corning 544 antifoam to IIT747 antifoam in the 1/240 SRAT", United States: N.p., 2000, Web, doi:10.2172/755212.
Lewis et al. "Cleaning, disinfection and sterilization of equipment." Anaesthesia and Intensive Care Medicine 5:11, 2004, pp. 360-363.
Sedlock et al., "Microbicidal Activity of Octenidine Hydrochloride, a New Alkanediylbis[Pyridine] Germicidal Agent", Antimicrobial Agents and Chemotherapy, Dec. 1985, pp. 786-790.
May 7, 2019 extended European Search Report issued in European Patent Application No. 16882754.1.

* cited by examiner

*Primary Examiner* — Michael P Cohen
(74) *Attorney, Agent, or Firm* — Arent Fox LLP

(57) ABSTRACT

A nonwoven wipe comprises an antiseptic solution comprising a bis-(dihydropyridinyl)-decane derivative, a first fiber having a denier of about 1.5 to about 2.0, and a second fiber having a denier of about 3.0 to 3.5. About 30 wt % to 70 wt % of the total weight of the nonwoven wipe is the first fiber and about 30 wt % to 70 wt % of the total weight of the nonwoven wipe is the second fiber. The bis-(dihydropyridinyl)-decane may be octenidine dihydrochloride.

19 Claims, No Drawings

ANTIMICROBIAL WIPE

CROSS-REFERENCE TO RELATED APPLICATION

This Application for Patent is a Continuation of U.S. patent application Ser. No. 14/985,042, titled "ANTIMICROBIAL WIPE", filed on Dec. 30, 2015, the entire contents of which are incorporated by reference herein.

FIELD OF THE INVENTION

Aspects of the present invention relate to the field antimicrobial wipes, and in particular a non-woven wipe soaked with an antiseptic solution.

BACKGROUND OF THE INVENTION

U.S. Pat. No. 7,427,574 to Allen discloses a non-woven washcloth formed from a blend of two different size polyester fibers, the majority of which have a length about half of that of the minority. The washcloth disclosed by Allen is particularly designed to have absorbing and holding properties for a non-alcoholic solution containing chlorhexidine gluconate (CHG), while also releasing the CHG when wiped on skin. As noted by Allen, a problem with CHG and CHG blends is that they tend to chemically or mechanically bind with certain fibers. Thus, Allen discloses a particular washcloth for use with CHG that purports to avoid such problems.

The washcloth of Allen being specially designed for a non-alcoholic CHG solution is not disclosed as suitable for use with other antiseptic solutions. Molecules other than CHG may be more potent and have other advantages over CHG.

U.S. Pat. No. 7,066,916 to Keaty, Jr. discloses a method of treating a patient prior to surgery using a cloth wipe soaked with a non-alcoholic CHG solution.

Thus, there is a need in the art for a wipe comprising an antiseptic solution having a more potent antiseptic.

SUMMARY OF THE INVENTION

Aspects of the present invention overcome the above identified problems, as well as others, by providing a wipe comprising an antiseptic solution comprising a bis-(dihydropyridinyl)-decane derivative, a first fiber having a denier of about 1.5 to about 2.0, and a second fiber having a denier of about 3.0 to 3.5. About 30 wt % to 70 wt % of the total weight of the wipe may be the first fiber and about 30 wt % to 70 wt % of the total weight of the wipe may be the second fiber. The bis-(dihydropyridinyl)-decane may be octenidine dihydrochloride.

The wipe may include a third fiber having a denier of about 5.0 to 6.0, wherein about 10 wt % to about 30 wt % of the total weight of the wipe is the third fiber. In an example aspect, about 40 wt % of the total number of fibers is the first fiber, about 40 wt % of the total weight of the wipe is the second fiber, and about 20 wt % of the total weight of the wipe is the third fiber. Each of the first, second, and third fiber may comprise polyester.

Aspects of the present invention include a package containing the wipe. The package may comprise a metal foil or a metalized plastic. The wipe may be sterilized by expositing the package containing the wipe to a temperature of about 110 to 130° C. for at time of about 15 to 30 minutes.

The package may further include a warming mechanism. The warming mechanism may comprise reactants that create an exothermic reaction when exposed to ambient air or when exposed to each other.

Additional advantages and novel features relating to aspects of the present invention will be set forth in part in the description that follows, and in part will become more apparent to those skilled in the art upon examination of the following or upon learning by practice thereof.

DETAILED DESCRIPTION

Various aspects of a wipe may be illustrated with reference to one or more exemplary embodiments. As used herein, the term "exemplary" means "serving as an example, instance, or illustration," and should not necessarily be construed as preferred or advantageous over other embodiments.

The term "about" as used herein preferably means±5% and more preferably ±1% of the provided value.

Aspects of the present invention include a wipe comprising an antiseptic solution. In an aspect of the present invention, the antiseptic solution is aqueous. That is, the solvent of the solution is primarily water. As used herein, aqueous means at least about 50% v/v or more water, more preferably at least about 60% v/v or more water, more preferably at least about 70% v/v or more water, more preferably at least about 80% v/v or more water, more preferably at least about 90% v/v or more water, more preferably at least about 95% v/v or more water, up to 100% v/v water. When the solution is less than 100% v/v water, the remaining volume may include one or more additional solvents, for example, alcoholic solvents. Example alcoholic solvents include ethanol, isopropanol, and n-propanol. For example, the solution may contain less than about 50% v/v, more preferably less than about 40% v/v, more preferably less than about 30% v/v, more preferably less than about 20% v/v, more preferably less than about 10% v/v, down to 0% v/v alcohol.

In another aspect of the present invention, the antiseptic solution is alcoholic, where the above solvent is primarily alcohol. When the solvent primarily comprises alcohol, there may be about 50% v/v or more alcohol, more preferably about 60% v/v or more alcohol, more preferably about 70% v/v or more alcohol, more preferably about 80% v/v or more alcohol, more preferably 90% v/v or more alcohol, more preferably about 95% v/v or more alcohol. When the solution comprises less than 100% v/v alcohol, the remaining volume may include one or more additional solvents, for example, water. Example alcoholic solvents include ethanol, isopropanol, and n-propanol. For example, the solution may contain less than about 50% v/v, more preferably less than about 40% v/v, more preferably less than about 30% v/v, more preferably less than about 20% v/v, more preferably less than about 10% v/v, down to 0% v/v water.

Suitable antiseptic molecules include bis-(dihydropyridinyl)-decane derivatives. As used herein, the term "derivative" refers to a) a chemical substance that is related structurally to a first chemical substance and derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. Preferred antiseptic agents include octenidine salts, such as octenidine dihydrochloride. The concentration of antiseptic molecule (e.g., octenidine dihydrochloride) may be from about 0.01% w/v to about 5.0% w/v, more preferably about 0.1% w/v to about 3.0% w/v, more preferably from about 0.2% w/v to about 1.0% w/v, and still more preferably from about 0.3% w/v to about 0.6% w/v. In one example aspect, the concentration of antiseptic molecule (e.g., octenidine dihydrochloride) may be 0.4% w/v. In another example, the concentration of antiseptic molecule (e.g., octenidine dihydrochloride) may be above 0.2% w/v. In an aspect of the present invention the bis-(dihydropyridinyl)-decane derivative (e.g., octenidine dihydrochloride) may be the only antimicrobial molecule present in the solution. In another aspect to of the present invention, the solution may include more than one antiseptic, for example, the solution may include a mixture of a bis-(dihydropyridinyl)-decane derivative (e.g., octenidine dihydrochloride) and a biguanide (e.g., chlorhexidine gluconate). In one example aspect the solution may include 2.0% w/v or less of a biguanide (e.g., chlorhexidine gluconate) and 1.0% w/v or less of a bis-(dihydropyridinyl)-decane derivative (e.g., octenidine dihydrochloride).

The wipe may contain additional components to enhance the effectiveness of the antiseptic solution when applied to a surface (e.g., human skin) via the wipe. For example, the wipe may contain non-active ingredients/agents with functions that include skin conditioning (e.g., moisturizing and skin smoothing), visualization, solubility, stability, viscosity, wetting, preservatives, etc. In an aspect of the present invention, the wipe may comprise one or more, including all, of the following additional components: from about 0.2% w/v to about 8.0% w/v, more preferably from about 2.0% w/v to about 5.0% w/v of a skin conditioner, from about 0.1% w/v to about 15% w/v, more preferably about 5.0% w/v to about 10.0% w/v of a preservative such as isopropyl alcohol, ethanol, and/or n-proponal, from about 0.01% w/v to about 3.0% w/v, more preferably about 0.05% w/v to about 2.0% w/v, and more preferably about 0.1% w/v to about 1.0% w/v of a antifoaming agent such as dimethicone (polydimethylsiloxane) e.g., dimethicone 350 cst, from about 0.1% w/v to about 5.0% w/v, more preferably about 0.5% w/v to about 3.0% w/v of a surfactant such as polyoxyl 40 hydrogenated castor oil, also known as macrogol-glycerolhydroxystearate (e.g., Cremophor® RH40; Kolliphor™ RH 40, each sold by BASF), about 0.01% w/v to about 0.2% w/v, more preferably from about 0.05% w/v to about 0.125% w/v of a surfactant such as nonoxynol-9 (α-(p-Nonylphenyl)-ω-hydroxynona(oxyethylene)), and from about 0.1% w/v to about 1.5% w/v, more preferably 0.5% w/v to about 1.0% w/v pH buffer salts.

In an aspect of the present invention, one or more of the above-listed components may be entirely omitted. For example, in one example aspect all alcohol may be omitted, i.e., no alcohol as solvent and no alcohol as a preservative.

The skin conditioner may comprise one or more compounds, for example about 0.1% w/v to about 5.0% w/v (relative to the overall solution), more preferably about 0.1% w/v to about 3.0% w/v of glycerin and about 0.1% w/v to about 3.0% w/v (relative to the overall solution), more preferably about 1.0% w/v to about 2.0% w/v of 1,3-propanediol. The buffer salts may comprise one or more buffer salts, to provide a desired solution overall pH. The buffer salts and concentrations of buffer salts may be chosen such that the solution has a pH of 4 to 7, more preferably 5.5 to 7, for example 6. Example buffer salts include monobasic potassium phosphate and dibasic sodium phosphate, and combinations thereof. As an alternative to polyoxyl 40 hydrogenated castor oil, polysorbate 20 (polyoxyethylene 20 sorbitan monolaurate), 60, and/or 80 may be used. The above components can be contained in the antiseptic solution. Alternatively, these above components can be added separately to the wipe.

The wipe to which the antiseptic solution and, optionally the additional components, may be applied, may be a non-woven fabric formed from a plurality of different polymer fibers. In an aspect of the present invention, the wipe may comprise two or more, more preferably three different polymer fiber types. In one example aspect the wipe comprises or consists of two different types of fibers and in another example aspect the wipe comprises or consists of three different types of fibers. The wipe may be formed using known nonwoven fabric manufacturing techniques. One such general process includes first defining the final density of the desired wipe (e.g., the grams per square meter (gsm) of the completed wipe), second homogenously blending the fibers together in a predetermined ratio including relative amounts sufficient to provide the defined density, third carding the blended fibers, fourth cross-lapping the carded fibers, and fifth needle punching the cross-lapped fibers. The needle punching serves as a method of mechanical entanglement of the blended fibers. Other suitable mechanical/thermal engagement methods known in the relevant art may also be used. As is known in the relevant art, needle punching involves punching fine barbed needles into the cross-lapped fibers which generally entangles fibers on the bottom of the cross-lapped fibers with fibers at the top. This technique of needle punching reduces the occurrence of pilling and linting in the completed nonwoven material.

In one example aspect of the present invention, the first type of fiber may be a polyester fiber having a denier of about 1.3 to about 2.0, more preferably 1.5, and the second type of fiber may be a polyester fiber having a denier of about 2.5 to about 3.5, more preferably 3.0. The length of both the first and second fiber types may be about 1.0 to 4.0 inches, more preferably 3.0 inches. About 30 wt % to about 70 wt %, more preferably about 40 wt % to about 50 wt % of the wipe may be the first fiber type. About 30 wt % to 70 wt %, more preferably about 40 wt % to about 50 wt % of the wipe may be the second fiber type. As noted above, in an aspect of the present invention, the wipe may consist only of these two fiber types. The polyester may comprise polyethylene terephthalate, which is sold for example under the brand name Dacron®.

As used herein, wt % means the weight of the particular fiber relative to the total weight of the final wipe material prior to soaking with solution. For example, if a given wipe material is 160 grams per square meter (gsm), and is 50 wt % of the first fiber and 50 wt % of the second fiber, then 80 gsm is attributable to the first fiber and 80 gsm is attributable to the second fiber.

In another aspect of the present invention, the wipe may include a third type of fiber in addition to the first and second fiber types. The third type of fiber may be a polyester fiber having a denier of about 5.0 to about 7.0 denier, more preferably 6.0 denier. Having the third fiber of 5.0 to about 7.0, more preferably 6.0 denier provides additional exfoliating properties to the wipe. Adding exfoliation properties increases the efficacy of the wipe by removing dead skin when it is being used to wipe the skin. The length of the third fiber type may also have a length of about 1.0 to about 4.0 inches, more preferably 3.0 inches. About 10 wt % to about 30 wt %, more preferably about 15 wt % to about 25 wt % of the wipe may be the third fiber type, in addition to the relative amounts of the first and second fiber types noted above. In an aspect of the present invention, the wipe may consist only of the three fiber types, in which case the relative amounts of the first, second, and third fiber types would be selected so that the total percentage of type one, type two, and type three together are 100 wt %. For example, 40 wt % of the wipe may be the first type, 40 wt % of the wipe may be the second type, and 20 wt % of the total number of fibers in the wipe may the third type.

The completed wipe may have a thickness of about 0.070 inches to about 0.110 inches, more preferably about 0.080 inches to about 0.100 inches, and more preferably about 0.085 inches to about 0.095 inches. The density may be about 130 grams per square meter (gsm) to about 175 gsm, more preferably about 140 gsm to about 165 gsm, and more preferably about 145 gsm to about 160 gsm. The wipe can be cut to a desired size depending on the use. For example, the wipe may be cut to an 8.0 inch by 8.0 inch square.

An 8.0 inch by 8.0 inch wipe having the above properties and comprising the above fibers was found to absorb about 20 to about 30 mL of the above-described antiseptic solution, with 25 mL being preferable. The wipe may absorb from about 0.3 mL of solution per square inch of wipe to about 0.4 mL of solution per square inch of wipe. The solution may be applied to the wipe by spraying the solution on the wipe, dipping the wipe into the solution or pouring the solution over the wipe until it is saturated, with spraying being preferred.

Once soaked with solution, the wipe may then be packaged. The package may be made of a material that sufficiently conducts heat while maintaining integrity to allow the wipe to be sterilized by heat sterilization when the package is exposed to a heat sterilization process. For example, the package material may be a metal foil (e.g., aluminum foil) or a metalized plastic (e.g., a metalized polyethylene terephthalate film). The thickness of the package material may be about 0.002 inches to 0.010 inches.

It has been found that when the above-described wipe is soaked with the above-described solution, and then the soaked wipe is applied to skin, the solution is released from the wipe and remains effective as an antimicrobial. Examples and experimental results are discussed below.

Once packaged, the wipe can be sterilized by exposing the entire package to a heat sterilization process. The heat sterilization process includes exposing the package with the wipe to a predetermined temperature (i.e., a sterilization temperature) for a predetermined period of time (i.e., a sterilization time). In an aspect of the present invention, the package can be exposed to a sterilization temperature from about 110° C. to about 135° C., more preferably 115° C. to about 130° C., and more preferably about 120° C. to about 125° C. For example, the sterilization temperature may be 121° C. The package may be exposed to the temperature for a time period of about 15 minutes to about 35 minutes, more preferably about 20 minutes to about 30 minutes. For example, the sterilization time may be 24 minutes. During the sterilization process, an overpressure may be applied sufficient to maintain the seal on the package and maintain the antiseptic solution in liquid form. For example, an overpressure of 2-3 bar may be used.

After sterilization, the antiseptic solution remains in the wipe and the antiseptic molecule remains sufficiently pure to maintain antimicrobial efficacy due in part to the stability of octenidine dihydrochloride. As used herein, purity means the percent concentration of antiseptic molecules in solution relative to the total concentration of antiseptic molecules plus concentration of substances that are derived from or related to the antiseptic molecule. For example, a 95% pure antiseptic solution means that if there are 100 molecules that are either antiseptic molecules or molecules derived from or related to the antiseptic molecule, 95 of the molecules are the antiseptic molecule and 5 of those molecules are derived from or related to the antiseptic molecule. These molecules derived from or relating to the antiseptic molecule have reduced or no antimicrobial activity. Thus, a lower purity solution will have lower antimicrobial efficacy as fewer of the target antiseptic molecules are delivered to the patient's skin. Further, a lower purity solution will not comply with regulatory requirements. By measuring the concentration of antiseptic molecules in solution as compared to concentration of antiseptic molecules and molecules derived from or related to the antiseptic molecule, one can determine the purity of the solution. The solution in the wipe following sterilization may be at least 95% pure, more preferably at least 96% pure, more preferably at least 97% pure, more preferably at least 98% pure, more preferably at least 99% pure, and most preferably 99.5% pure. In other words, the percent of impurities derived from the antiseptic molecule (e.g., octenidine dihydrochloride) relative to total number of impurities plus antiseptic molecules may be 5% or less, more preferably 4% or less, more preferably 3% or less, more preferably 2% or less, more preferably 1% or less, and most preferably 0.5% or less.

It is believed that by heating the antiseptic solution contained in the wipe to the above sterilization temperatures and maintaining the temperature for the above sterilization times, sufficiently sterilizes the solution, while maintaining sufficient antimicrobial efficacy. The amount of degradation of the antiseptic molecule can be quantified by measuring the initial purity of antiseptic solution prior to the sterilization process and measuring the post-sterilized purity of antiseptic solution after the sterilization process. Thus, as used herein, the "initial purity" is the purity prior to sterilization and "post-sterilization purity" is the purity of the solution after sterilization once the wipe has reached room temperature.

Octenidine dihydrochloride molecules may degrade into one or more of the following molecules when heat treated: N,N'-(decane-1(pyridine-1-yl-4-ylidene)octan-1-amine)-10, (4-hydroxypyridine) (IUPAC name: 1-{10-[4-(Octylimino)-1H-pyrid-1-yl]decyl}-1H-pyridin-4-one; molecular formula: $C_{28}H_{45}N_3O$; Formula I) and decane-1(pyridine-1-yl-4-ylindene)octan-1-amine)-10-ol (IUPAC name: 10-[4-(Octylimino)-1H-pyrid-1-yl]decanol; molecular formula: $C_{23}H_{42}N_2O$; Formula II).

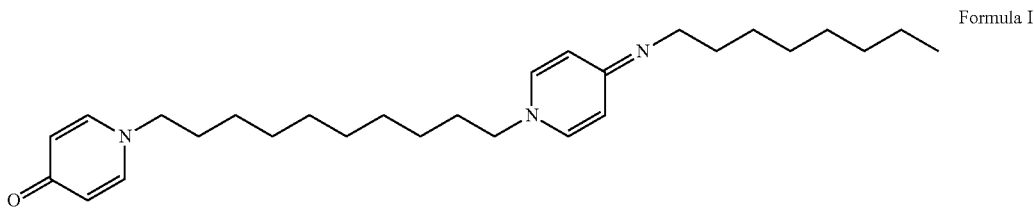

Formula I

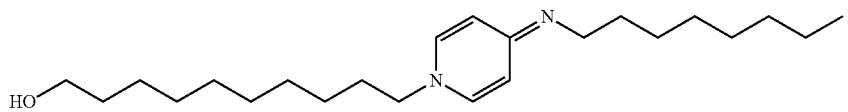

Formula II

Thus, the purity of the solution can be determined by comparing the amount of octenidine dihydrochloride molecules to all of the above-listed octenidine dihydrochloride related substances. However, it should be noted that the above list is not exhaustive. One having ordinary skill in the art would be able to determine which molecules are degradants of the antiseptic molecule after the sterilization process.

The combination of sterilization temperature and sterilization time may be chosen such that the percentage point change in purity from the initial purity to the post-sterilization purity is at most about 5%, more preferably at most about 3%, more preferably at most about 2%, and most preferably at most about 1%. It should be understood that the percentage point change refers to the absolute percentage point difference between the initial purity and the post-sterilization purity. For example, a change in initial purity of 95% to a post-sterilization purity of 90% is a percentage point change of 5%.

It is within the scope of the invention that any machine capable of heating the wipe with antiseptic solution to the sterilization temperature and maintaining the wipe with solution at the sterilization temperature for the sterilization time may be used. Example equipment may include a water bath, oil bath, autoclave, convection oven, cascading water sterilizer, and the like. A cascading water sterilizer provides a constant stream of water which heats the solution to the sterilization temperature, maintains the sterilization temperature over the entirety of the sterilization time, and finally cools the solution.

In another aspect of the present invention, it is desirable for the wipe to be heated to a comfortable temperature just prior to use on a patient. This can be achieved in a variety of ways. In one example, the practitioner can place the package with wipes into a separate warming device, such as an electrically powered warming cabinet. The metalized plastic package can also be heated in a microwave. More preferably, however, to avoid the need for a separate warming device, the package containing the wipe may include (internally or externally) a warming mechanism that provides an on-demand exothermic (chemical or physical) reaction. The exothermic reaction produces heat to warm the wipe without reacting with or otherwise affecting the antiseptic solution. For example the portable heater described in U.S. Pat. App. Pub. No. 2010/0146849 comprises a particulate composite fuel that reacts with oxygen in the air to produce heat, a thermal conductive member, and an insulating member. Other suitable warming mechanisms are described in U.S. Pat. App. Pub. Nos. 2010/0163011, 2010/0326418, 2013/0174835, 2014/0102435, 2014/01809889, 2014/0109890. Each of the preceding documents is expressly incorporated by reference herein in their entirety.

In an aspect of the present invention, any of the above noted warming mechanisms may be specifically tailored so that the user can initiate the reaction by removing a strip, cover, or sticker which exposes one or more reactants to the ambient environment. Alternatively, the user may expose one or more reactants which are all contained in the package to each other to initiate the heat-generating reaction, without exposing the reactants to ambient environment. Other examples of reaction initiators may include turning a dial, pressing a button, snapping or breaking a reaction initiator, and/or physical manipulation of the package (e.g. folding, shaking, squeezing, or twisting). In these cases the wipe is heated before the package is opened. Alternatively, the reaction may be initiated by the process of opening the package itself. The reaction may be particularly tailored such that the wipes reach a temperature of about 100° F. to about 125° F. within about 1 to about 2 minutes. Preferably, the reaction may be tailored to reach 125° F. within 1 minute. Alternatively, the user may choose the desired final temperature by activating a specific section of the package to initiate varying degrees of the exothermic reaction. For example, a first final temperature could be obtained by removal of one strip, while a second final temperature could be obtained by removal of a second strip. To this end, other mechanisms mentioned above for initiation of the exothermic reaction could be similarly modified to allow varying degrees of heating or choice between discrete final temperatures.

EXAMPLES

Example 1

A wipe was prepared using a blend of a first polyester fiber having a denier of 1.5 and a length of 1.5 inches and a second polyester fiber having a denier of 3.0 and a length of 3.0 inches. 50 wt % of the wipe was the first polyester fiber and 50 wt % of the wipe was the second polyester fiber. The wipe was prepared using the manufacturing method described above including needle punching. The amount of each fiber was loaded per square meter to provide a completed wipe density of 160 gsm. Thus, 80 gsm of the wipe weight was attributed to the first fiber and 80 gsm of the wipe weight was attributed to the second fiber. The produced wipe had a thickness of 0.090 inches. The wipe was soaked with an antiseptic solution. The solution contained 0.4% w/v octenidine dihydrochloride, 1.5% w/v glycerin, 1.5% w/v 1,3-propanediol, 0.0875% w/v dimethicone, 0.50% w/v polysorbate 20, 0.06% w/v Nonoxynol-9, 0.62% w/v Monobasic Potassium Phosphate, 0.07% w/v salt Dibasic Sodium Phosphate, and the remainder water. The wipe absorbed 25 mL of solution.

Example 2

The same wipe of Example 1 was prepared. The wipe was soaked with an antiseptic solution. The solution contained 0.4% w/v octenidine dihydrochloride, 1.5% w/v glycerin, 1.5% w/v 1,3-propanediol, 0.0875% w/v dimethicone, 0.125% w/v Nonoxynol-9, 0.50% w/v Cremophor® RH40, 0.62% w/v pH 6 buffer slat Monobasic Potassium Phosphate, 0.07% w/v pH 6 buffer salt Dibasic Sodium Phosphate, and the remainder water. The wipe absorbed 25 mL of solution.

Example 3

A wipe was prepared using a blend of a first polyester fiber having a denier of 1.5 and a length of 3.0 inches and a second polyester fiber having a denier of 3.0 and a length of 3.0 inches. 50 wt % of the wipe was the first polyester fiber and 50 wt % of the wipe was the second polyester fiber. The same manufacturing method of Example 1 was used except that the degree of needle punching was increased so that the amount of mechanical entanglement in wipe was increased by 25% as compared to the wipe of Example 1. The resulting wipe has the same relative amount of fibers as Example 1 but had a thickness of 0.085 inches. The wipe was soaked with the same antiseptic solution of Example 2.

Example 4

The same wipe of Example 3 was prepared. The wipe was soaked with the same antiseptic solution of Example 1.

Example 5

The same wipe of Example 3 was prepared. The wipe was soaked with a solution containing 0.4% w/v octenidine dihydrochloride, 1.5% w/v glycerin, 1.5% w/v 1,3-propanediol, 0.0875% w/v dimethicone, 0.125% w/v Nonoxynol-9, 0.50% w/v polysorbate 20, 0.62% w/v pH 6 buffer slat Monobasic Potassium Phosphate, 0.07% w/v pH 6 buffer salt Dibasic Sodium Phosphate, and the remainder water.

Comparative Example 6

A wipe having 2% w/v chlorhexidine gluconate solution soaked therein was obtained from Sage Product Inc., having National Drug Code (NDC) number 53462-705-23.

Example 7

A wipe was prepared using a blend of a first polyester fiber having a denier of 1.5 and a length of 1.5 inches, a second polyester fiber having a denier of 3.0 and a length of 3.0 inches, and a third polyester fiber having a denier of 6.0 and a length of 3.0 inches. 40 wt % of the wipe was the first polyester fiber, 40 wt % of the wipe was the second polyester fiber, and 20 wt % of wipe was the third polyester fiber. The wipe was prepared using the manufacturing method described above including needle punching. The amount of each fiber was loaded per square meter to provide a completed wipe density of 160 gsm. Thus, 64 gsm of the wipe weight was attributed to the first fiber and 64 gsm of the wipe weight was attributed to the second fiber, and 32 gsm was attributed to the third fiber. The produced wipe has a thickness of 0.090 inches. The same antiseptic solution of Example 1 was soaked into the wipe.

Example 8

A wipe was prepared using a blend of a first polyester fiber having a denier of 1.5 and a length of 3.0 inches, a second polyester fiber having a denier of 3.0 and a length of 3.0 inches, and a third polyester fiber having a denier of 6.0 and a length of 3.0 inches. 40 wt % of the wipe was the first polyester fiber, 40 wt % of the wipe was the second polyester fiber, and 20 wt % of wipe was the third polyester fiber. The wipe was manufactured the same as Example 7, except that the degree of needle punching was increased so that the amount of mechanical entanglement in wipe was increased by 25% as compared to the wipe of Example 7. The resulting wipe had a thickness of 0.085 inches. The wipe was soaked with the same antiseptic solution of Example 1.

Example 9

The same wipe of Example 7 was prepared. The wipe was soaked with the solution of Example 2.

Example 10

The same wipe of Example 8 was prepared. The wipe was soaked with the solution of Example 2.

Example 11

A wipe was prepared using a blend of a first polyester fiber having a denier of 1.5 and a length of 1.5 inches and a second polyester fiber having a denier of 3.0 and a length of 3.0 inches. 50 wt % of the wipe was the first polyester fiber and 50 wt % of the wipe was the second polyester fiber. The wipe was prepared using the manufacturing method described above including needle punching. The amount of each fiber was loaded per square meter to provide a completed wipe density of 145 gsm. Thus, 72.5 gsm of the wipe weight was attributed to the first fiber and 72.5 gsm of the wipe weight was attributed to the second fiber. The produced wipe had a thickness of 0.085 inches. The same antiseptic solution of Example 1 was soaked into the wipe.

Example 12

A wipe was prepared using a blend of a first polyester fiber having a denier of 1.5 and a length of 1.5 inches, a second polyester fiber having a denier of 3.0 and a length of 3.0 inches, and a third polyester fiber having a denier of 6.0 and a length of 3.0 inches. 40 wt % of the wipe was the first polyester fiber, 40 wt % of the wipe was the second polyester fiber, and 20 wt % of wipe was the third polyester fiber. The wipe was prepared using the manufacturing method described above including needle punching. The amount of each fiber was loaded per square meter to provide a completed wipe density of 145 gsm. Thus, 58 gsm of the wipe weight was attributed to the first fiber and 58 gsm of the wipe weight was attributed to the second fiber, and 29 gsm was attributed to the third fiber. The produced wipe has a thickness of 0.085 inches. The same antiseptic solution of Example 1 was soaked into the wipe.

Comparative Example P1

The same wipe of Example 3 was prepared. The wipe was soaked with a solution containing 1.5% w/v glycerin, 1.5% w/v 1,3-propanediol, 0.0875% w/v dimethicone, 0.06% w/v Nonoxynol-9, 0.50% w/v polysorbate 20, 0.62% w/v pH 6 buffer slat Monobasic Potassium Phosphate, 0.07% w/v pH 6 buffer salt Dibasic Sodium Phosphate, and the remainder water. Notably, no antiseptic was included.

Example P2

The same wipe of Example 3 was prepared. The wipe was soaked with a solution containing 0.4% w/v octenidine dihydrochloride, 1.5% w/v glycerin, 1.5% w/v 1,3-propanediol, 0.0875% w/v dimethicone, 0.06% w/v Nonoxynol-9, 0.50% w/v polysorbate 20, 0.62% w/v pH 6 buffer slat Monobasic Potassium Phosphate, 0.07% w/v pH 6 buffer salt Dibasic Sodium Phosphate, and the remainder water Example P3

The same wipe of Example 3 was prepared. The wipe was soaked with a solution containing 0.4% w/v octenidine dihydrochloride, 1.5% w/v glycerin, 1.5% w/v 1,3-propanediol, 0.0875% w/v dimethicone, 0.06% w/v Nonoxynol-9, 0.50% w/v Cremophor® RH-40, 0.62% w/v pH 6 buffer slat Monobasic Potassium Phosphate, 0.07% w/v pH 6 buffer salt Dibasic Sodium Phosphate, and the remainder water.

D-Value Determination

The D-value for a microorganism is the time required to reduce its population by 90% at a specified temperature and substrate condition, and the value is used in the art to establish a sterilization time. Thus after a colony is reduced by 1 D, only 10% of the original organisms remain, i.e., the population number has been reduced by one decimal place in the counting scheme. D-values can be calculated using the Survivor Curve Method described in ISO 11138-1:2006, Annex C.

A 4.0 inch×4.0 inch polyester wipe of Example 1 was soaked with 6 mL of an antiseptic solution consisting of 0.4% w/v octenidine dihydrochloride dissolved in water and innocluated with approximately $10^7$ colony-forming units (CFU) of *Geobacillus stearothermophilus* spores. The soaked sample was enclosed in an aluminum foil pouch and heat sealed. The pouch was then exposed to 121° C. heat for 5.0, 10.0 and 15.0 minutes in a steam vessel. The above steps were duplicated four times for each exposure time. Four samples were also tested that were not exposed to the heat.

A population assay was performed on the wipes. The Colony Forming Unit (CFU) counts from population assays performed on exposed and unexposed wipes are presented in Tables 1 through 4.

TABLE 1

| | Exposure Time (minutes) | | | | | | | |
|---|---|---|---|---|---|---|---|---|
| Dilution | 0.0 (#1) CFU Count | | 0.0 (#2) CFU Count | | 0.0 (#3) CFU Count | | 0.0 (#4) CFU Count | |
| $10^{-4}$ | TNTC | TNTC | TNTC | TNTC | TNTC | TNTC | TNTC | TNTC |
| $10^{-5}$ | 42 | 35 | 46 | 40 | 34 | 51 | 55 | 43 |

TABLE 2

| | Exposure Time (minutes) | | | | | | | |
|---|---|---|---|---|---|---|---|---|
| Dilution | 5.0 (#1) CFU Count | | 5.0 (#2) CFU Count | | 5.0 (#3) CFU Count | | 5.0 (#4) CFU Count | |
| $10^{-2}$ | 4 | 6 | 5 | 3 | 5 | 3 | 2 | 4 |
| $10^{-3}$ | 3 | 2 | 2 | 1 | 2 | 1 | 0 | 0 |
| $10^{-4}$ | 0 | 0 | 0 | 0 | 0 | 0 | 0 | 0 |
| $10^{-5}$ | 0 | 0 | 0 | 0 | 0 | 0 | 0 | 0 |

TABLE 3

| | Exposure Time (minutes) | | | | | | | |
|---|---|---|---|---|---|---|---|---|
| Dilution | 10.0 (#1) CFU Count | | 10.0 (#2) CFU Count | | 10.0 (#3) CFU Count | | 10.0 (#4) CFU Count | |
| $10^{-2}$ | 1 | 1 | 1 | 1 | 0 | 0 | 0 | 0 |
| $10^{-3}$ | 0 | 0 | 0 | 0 | 0 | 0 | 0 | 0 |
| $10^{-4}$ | 0 | 0 | 0 | 0 | 0 | 0 | 0 | 0 |

TABLE 4

| | Exposure Time (minutes) | | | | | | | |
|---|---|---|---|---|---|---|---|---|
| Dilution | 15.0 (#1) CFU Count | | 15.0 (#2) CFU Count | | 15.0 (#3) CFU Count | | 15.0 (#4) CFU Count | |
| $10^{-2}$ | 0 | 0 | 0 | 0 | 0 | 0 | 0 | 0 |
| $10^{-3}$ | 0 | 0 | 0 | 0 | 0 | 0 | 0 | 0 |

Using the CFU count data presented in Tables 1-4, the population of *G. stearothermophilus* spores in the exposed and unexposed units of inoculated polyester wipes was calculated. Based on the average population determined from each exposure time, a survivor curve following the Survivor Curve Method was created and a $D_{121}$-value of 2.0 minutes was calculated based on a survivor curve with an $r^2$ of 0.9269.

The above process may also be used to find the D value for other sterilization temperatures.

Antimicrobial Efficacy

Examples P1-P3 and 6 were tested for antimicrobial efficacy. For each example, five 7"×7" sections of pig skin were prepared and each delineated with a 5"×5" treatment and evaluation area. Each of the pig skin sections was inoculated with a known population of *Staphylococcus epidermidis* and allowed to dry at 36.1° C.-36.2° C., with a relative humidity of 90%-92% for 30 minutes. After drying, each inoculated section was sampled using standard cup scrub methodology to measure the baseline. After the baseline, the examples were applied to each of the inoculated sections using a back and forth motion for 3-minutes (each wipe was turned over and re-folded after 1 minute 30 seconds) and allowed to dry for 1-minute. After contact times of 30 seconds and 10 minutes post-prep, a specific area was sampled in the same manner as the baseline. Each sample was serially diluted and selected aliquots were plated. All plates were incubated at 36±1° C. for 48±2 hours. The results are shown in the below tables.

TABLE 5

| | Example P3 | | | | |
|---|---|---|---|---|---|
| Replicate | Sample | Average CFU per mL | CFU/ cm²* | $Log_{10}$ CFU/ cm² | $Log_{10}$ Reduction/ cm² |
| 1 | Baseline | $1.7 \times 10^5$ | $2.7 \times 10^5$ | 5.43 | NA |
| | 30 seconds | $1.5 \times 10^2$ | $2.4 \times 10^2$ | 2.38 | 3.05 |
| | 10 minutes | $5.4 \times 10^2$ | $8.5 \times 10^2$ | 2.93 | 2.50 |
| 2 | Baseline | $1.2 \times 10^5$ | $1.9 \times 10^5$ | 5.28 | NA |
| | 30 seconds | $1.2 \times 10^3$ | $1.9 \times 10^3$ | 3.28 | 2.00 |
| | 10 minutes | $1.4 \times 10^2$ | $2.2 \times 10^2$ | 2.34 | 2.94 |
| 3 | Baseline | $8.6 \times 10^4$ | $1.4 \times 10^5$ | 5.15 | NA |
| | 30 seconds | $8.5 \times 10^2$ | $1.3 \times 10^3$ | 3.11 | 2.04 |
| | 10 minutes | $3.5 \times 10^2$ | $5.5 \times 10^2$ | 2.74 | 2.41 |

TABLE 5-continued

Example P3

| Replicate | Sample | Average CFU per mL | CFU/ cm²* | $Log_{10}$ CFU/ cm² | $Log_{10}$ Reduction/ cm² |
|---|---|---|---|---|---|
| 4 | Baseline | $1.3 \times 10^5$ | $2.1 \times 10^5$ | 5.32 | NA |
|   | 30 seconds | $6.2 \times 10^2$ | $9.8 \times 10^2$ | 2.99 | 2.33 |
|   | 10 minutes | $2.0 \times 10^2$ | $3.2 \times 10^2$ | 2.51 | 2.81 |
| 5 | Baseline | $1.7 \times 10^5$ | $2.7 \times 10^5$ | 5.43 | NA |
|   | 30 seconds | $7.7 \times 10^1$ | $1.2 \times 10^2$ | 2.08 | 3.35 |
|   | 10 minutes | $1.8 \times 10^1$ | $2.8 \times 10^1$ | 1.45 | 3.98 |

TABLE 6

Example P2

| Replicate | Sample | Average CFU per mL | CFU/ cm²* | $Log_{10}$ CFU/ cm² | $Log_{10}$ Reduction/ cm² |
|---|---|---|---|---|---|
| 1 | Baseline | $2.1 \times 10^5$ | $3.3 \times 10^5$ | 5.52 | NA |
|   | 30 seconds | $1.6 \times 10^2$ | $2.5 \times 10^2$ | 2.40 | 3.12 |
|   | 10 minutes | $2.1 \times 10^1$ | $3.3 \times 10^1$ | 1.51 | 4.01 |
| 2 | Baseline | $1.6 \times 10^5$ | $2.5 \times 10^5$ | 5.40 | NA |
|   | 30 seconds | $1.5 \times 10^3$ | $2.4 \times 10^3$ | 3.38 | 2.02 |
|   | 10 minutes | $8.0 \times 10^1$ | $1.3 \times 10^2$ | 2.11 | 3.29 |
| 3 | Baseline | $1.5 \times 10^5$ | $2.4 \times 10^5$ | 5.38 | NA |
|   | 30 seconds | $5.7 \times 10^2$ | $9.0 \times 10^2$ | 2.95 | 2.43 |
|   | 10 minutes | $1.4 \times 10^2$ | $2.2 \times 10^2$ | 2.34 | 3.04 |
| 4 | Baseline | $7.9 \times 10^4$ | $1.2 \times 10^5$ | 5.08 | NA |
|   | 30 seconds | $3.5 \times 10^2$ | $5.5 \times 10^2$ | 2.74 | 2.34 |
|   | 10 minutes | $1.9 \times 10^2$ | $3.0 \times 10^2$ | 2.48 | 2.60 |
| 5 | Baseline | $1.7 \times 10^5$ | $2.7 \times 10^5$ | 5.43 | NA |
|   | 30 seconds | $4.7 \times 10^1$ | $7.4 \times 10^1$ | 1.87 | 3.56 |
|   | 10 minutes | $1.4 \times 10^1$ | $2.2 \times 10^1$ | 1.34 | 4.09 |

TABLE 7

Comparative Example P1

| Replicate | Sample | Average CFU per mL | CFU/ cm²* | $Log_{10}$ CFU/ cm² | $Log_{10}$ Reduction/ cm² |
|---|---|---|---|---|---|
| 1 | Baseline | $2.1 \times 10^5$ | $3.3 \times 10^5$ | 5.52 | NA |
|   | 30 seconds | $1.1 \times 10^4$ | $1.7 \times 10^4$ | 4.23 | 1.29 |
|   | 10 minutes | $1.2 \times 10^4$ | $1.9 \times 10^4$ | 4.28 | 1.24 |
| 2 | Baseline | $2.3 \times 10^5$ | $3.6 \times 10^5$ | 5.56 | NA |
|   | 30 seconds | $3.2 \times 10^4$ | $5.1 \times 10^4$ | 4.71 | 0.85 |
|   | 10 minutes | $5.8 \times 10^3$ | $9.2 \times 10^3$ | 3.96 | 1.60 |
| 3 | Baseline | $1.7 \times 10^5$ | $2.7 \times 10^5$ | 5.43 | NA |
|   | 30 seconds | $8.2 \times 10^3$ | $1.3 \times 10^4$ | 4.11 | 1.32 |
|   | 10 minutes | $1.3 \times 10^4$ | $2.1 \times 10^4$ | 4.32 | 1.11 |
| 4 | Baseline | $1.7 \times 10^5$ | $2.7 \times 10^5$ | 5.43 | NA |
|   | 30 seconds | $1.3 \times 10^4$ | $2.1 \times 10^4$ | 4.32 | 1.11 |
|   | 10 minutes | $1.8 \times 10^4$ | $2.8 \times 10^4$ | 4.45 | 0.98 |
| 5 | Baseline | $1.1 \times 10^5$ | $1.7 \times 10^5$ | 5.23 | NA |
|   | 30 seconds | $3.9 \times 10^3$ | $6.2 \times 10^3$ | 3.79 | 1.44 |
|   | 10 minutes | $3.3 \times 10^3$ | $5.2 \times 10^3$ | 3.72 | 1.51 |

TABLE 8

Comparative Example 6

| Replicate | Sample | Average CFU per mL | CFU/ cm²* | $Log_{10}$ CFU/ cm² | $Log_{10}$ Reduction/ cm² |
|---|---|---|---|---|---|
| 1 | Baseline | $1.6 \times 10^5$ | $2.5 \times 10^5$ | 5.40 | NA |
|   | 30 seconds | $1.2 \times 10^3$ | $1.9 \times 10^3$ | 3.28 | 2.12 |
|   | 10 minutes | $8.6 \times 10^2$ | $1.4 \times 10^3$ | 3.15 | 2.25 |
| 2 | Baseline | $1.6 \times 10^5$ | $2.5 \times 10^5$ | 5.40 | NA |
|   | 30 seconds | $5.3 \times 10^2$ | $8.4 \times 10^2$ | 2.92 | 2.48 |
|   | 10 minutes | $4.6 \times 10^1$ | $7.3 \times 10^1$ | 1.86 | 3.54 |
| 3 | Baseline | $1.6 \times 10^5$ | $2.5 \times 10^5$ | 5.40 | NA |
|   | 30 seconds | $3.2 \times 10^2$ | $5.1 \times 10^2$ | 2.71 | 2.69 |
|   | 10 minutes | $1.4 \times 10^2$ | $2.2 \times 10^2$ | 2.34 | 3.06 |
| 4 | Baseline | $1.9 \times 10^5$ | $3.0 \times 10^5$ | 5.48 | NA |
|   | 30 seconds | $9.8 \times 10^2$ | $1.5 \times 10^3$ | 3.18 | 2.30 |
|   | 10 minutes | $7.9 \times 10^2$ | $1.2 \times 10^3$ | 3.08 | 2.40 |
| 5 | Baseline | $9.6 \times 10^4$ | $1.5 \times 10^5$ | 5.18 | NA |
|   | 30 seconds | $2.7 \times 10^1$ | $4.3 \times 10^1$ | 1.63 | 3.55 |
|   | 10 minutes | $1.6 \times 10^1$ | $2.5 \times 10^1$ | 1.40 | 3.78 |

TABLE 9

30 Seconds Contact Time

| Test Article | $Log_{10}$ Reduction per Replicate | | Average $Log_{10}$ Reduction |
|---|---|---|---|
| Example P3 | Replicate 1 | 3.05 | 2.55 |
|   | Replicate 2 | 2.00 |   |
|   | Replicate 3 | 2.04 |   |
|   | Replicate 4 | 2.33 |   |
|   | Replicate 5 | 3.35 |   |
| Example P2 | Replicate 1 | 3.12 | 2.69 |
|   | Replicate 2 | 2.02 |   |
|   | Replicate 3 | 2.43 |   |
|   | Replicate 4 | 2.34 |   |
|   | Replicate 5 | 3.56 |   |
| Comparative Example P1 | Replicate 1 | 1.29 | 1.20 |
|   | Replicate 2 | 0.85 |   |
|   | Replicate 3 | 1.32 |   |
|   | Replicate 4 | 1.11 |   |
|   | Replicate 5 | 1.44 |   |
| Comparative Example 6 | Replicate 1 | 2.12 | 2.63 |
|   | Replicate 2 | 2.48 |   |
|   | Replicate 3 | 2.69 |   |
|   | Replicate 4 | 2.30 |   |
|   | Replicate 5 | 3.55 |   |

TABLE 10

10 Minutes Contact Time

| Test Article | $Log_{10}$ Reduction per Replicate | | Average $Log_{10}$ Reduction |
|---|---|---|---|
| Example P3 | Replicate 1 | 2.50 | 2.93 |
|   | Replicate 2 | 2.94 |   |
|   | Replicate 3 | 2.41 |   |
|   | Replicate 4 | 2.81 |   |
|   | Replicate 5 | 3.98 |   |
| Example P2 | Replicate 1 | 4.01 | 3.41 |
|   | Replicate 2 | 3.29 |   |
|   | Replicate 3 | 3.04 |   |
|   | Replicate 4 | 2.60 |   |
|   | Replicate 5 | 4.09 |   |
| Comparative Example P1 | Replicate 1 | 1.24 | 1.29 |
|   | Replicate 2 | 1.60 |   |
|   | Replicate 3 | 1.11 |   |
|   | Replicate 4 | 0.98 |   |
|   | Replicate 5 | 1.51 |   |

TABLE 10-continued

10 Minutes Contact Time

| Test Article | Log$_{10}$ Reduction per Replicate | | Average Log$_{10}$ Reduction |
|---|---|---|---|
| Comparative Example 6 | Replicate 1 | 2.25 | 3.01 |
| | Replicate 2 | 3.54 | |
| | Replicate 3 | 3.06 | |
| | Replicate 4 | 2.40 | |
| | Replicate 5 | 3.78 | |

As shown from the above data, the CFU/cm$^2$ recovered from the artificially contaminated pig skin substrate using *Staphylococcus epidermidis*, Example P3, Example P2 and Comparative Example 6 achieved at least a 2.5 log reduction at the 30 second and 10 minute sampling time points. The CFU/cm$^2$ recovered from the artificially contaminated pig skin substrate using *Staphylococcus epidermidis*, Comparative Example P1 did not meet the proposed 2.5 log reduction at the 30 second and 10 minute sampling time points.

Octenidine dihydrochloride is a cationic antimicrobial agent with potent microbicidal activity against a broad range of microorganisms. However, being cationic in nature, octenidine dihydrochloride has a tendency to interact with anionic or nonionic surfactants (surface active agents) significantly decreasing its potency. Surface active agents may be added to antiseptic and cleaning products to provide hygiene benefits and to aid in the overall microbicidal effect of a product. The solutions used in wipes may contain multiple excipients that can potentially interact with octenidine dihydrochloride resulting in reduced efficacy.

Multiple surfactants in solution formulations were tested for use with the wipes. Effects of individual excipients such as phosphate buffer, polysorbate 20, nonoxynol-9, Cremophor® RH-40, dimethicone, and combinations of these products were investigated to determine the possibility of adverse effects on the antimicrobial efficacy of octenidine dihydrochloride. Bactericidal activities of octenidine dihydrochloride alone and in combinations with various excipients (Table 11) were tested by a time kill method using *Staphylococcus aureus* ATCC 29213 as test organism (Table 12).

TABLE 11

Compositions of formulations with Nonoxynol-9 and polysorbate 20

| Full base formulation | with Nonoxynol-9 | with Polysorbate 20 |
|---|---|---|
| Glycerin | 1.50% | 1.50% |
| 1,3-Propanediol | 1.50% | 1.50% |
| Dimethicone USP | 0.05% | 0.05% |
| Polysorbate 20 | 0.50% | 1.50% |
| Nonoxynol-9 | 0.10% | 0% |
| Na$_2$HPO$_4$ | 0.62% | 0.62% |
| KH$_2$PO$_4$ | 0.06% | 0.06% |

All percent values are w/v

TABLE 12

Effect of excipients on the potency of Octenidine Dihydrochloride (OCT)

| Base Formulation or Vehicle | OCT Conc. (PPM) | Log Reduction | Standard Deviation |
|---|---|---|---|
| Water | 2 | 3.41 | 0.15 |
| | 20 | 3.78 | 0.15 |
| | 100 | 4.65 | 0.21 |
| | 500 | 5.12 | 0.06 |
| Phosphate Buffered Water, pH 6.0 | 2 | 1.39 | 0.16 |
| | 20 | 2.87 | 0.28 |
| | 100 | 4.78 | 0.26 |
| | 500 | 5.12 | 0.06 |
| 1.5% Polysorbate 20 in water | 2 | 0.30 | 0.13 |
| | 20 | 0.57 | 0.11 |
| | 100 | 1.01 | 0.11 |
| | 500 | 1.12 | 0.21 |
| 0.1% Nonoxynol-9 in water | 2 | 1.52 | 0.19 |
| | 20 | 2.94 | 0.12 |
| | 100 | 4.69 | 0.32 |
| | 500 | 5.12 | 0.06 |
| 0.25% Dimethicone in water | 2 | 1.17 | 0.11 |
| | 20 | 1.41 | 0.11 |
| | 100 | 1.67 | 0.13 |
| | 500 | 2.12 | 0.07 |
| Full base formulation with Polysorbate 20 | 2 | 0.04 | 0.11 |
| | 20 | 0.35 | 0.12 |
| | 100 | 0.49 | 0.14 |
| | 500 | 0.76 | 0.07 |
| Full base formulation with Nonoxynol-9 and Polysorbate 20 | 2 | 0.29 | 0.23 |
| | 20 | 0.58 | 0.14 |
| | 100 | 0.60 | 0.14 |
| | 500 | 1.40 | 0.10 |
| | 1000 | 3.94* | 0.35 |
| | 2000 | 4.14* | 0.07 |
| | 4000 | 4.14* | 0.07 |

*Total kill was achieved; log reduction, calculated as the limit of detection, are reported.

As shown in Table 12, octenidine dihydrochloride alone, at a concentration as low as 2 PPM and a contact time of 30 seconds, caused rapid loss in bacterial viability resulting in >99.9% reduction in viable count. Octenidine dihydrochloride dissolved in pH 6.0 phosphate buffered water required >20 PPM (>10 times the concentration in water) to showed 99.9% reduction in viable count. Polysorbate 20, dimethicone and nonoxynol-9 were found to have significant neutralizing effects on the bactericidal activity of OCT up to a concentration of 500 PPM. However, higher than 1000 PPM of octenidine dihydrochloride in the full base formulation was found to be rapidly microbicidal. The "full base formulation" is the formulation defined in Table 11.

Neutralizing effects of two similar surfactants, 0.5% Cremophor® RH40 and 0.5% polysorbate 20, on the bactericidal activity of octenidine dihydrochloride were tested using the *Staphylococcus aureus* ATCC 29213 as test organism (Table 13 and 14).

TABLE 13

Adverse effects of Cremophor ® RH40 and Polysorbate 20 on bactericidal activity of octenidine dihydrochloride

| Formulation | OCT Conc. in PPM | Average Log | Average Log Reduction | Standard Deviation | Percent Reduction |
|---|---|---|---|---|---|
| Aqueous | 20 | 2.000 | 5.123 | 0.066 | 99.999 |
| | 100 | 2.000 | 5.123 | 0.066 | 99.999 |
| | 500 | 2.000 | 5.123 | 0.066 | 99.999 |

TABLE 13-continued

Adverse effects of Cremophor ® RH40 and Polysorbate 20
on bactericidal activity of octenidine dihydrochloride

| Formulation | OCT Conc. in PPM | Average Log | Average Log Reduction | Standard Deviation | Percent Reduction |
|---|---|---|---|---|---|
| 0.5% Cremophor ® RH40 | 20 | 6.383 | 0.740 | 0.310 | 81.808 |
|  | 100 | 5.651 | 1.472 | 0.155 | 96.624 |
|  | 500 | 2.000 | 5.123 | 0.066 | 99.999 |
| 0.5% Polysorbate 20 | 20 | 6.327 | 0.795 | 0.140 | 83.979 |
|  | 100 | 5.917 | 1.205 | 0.236 | 93.767 |
|  | 500 | 4.043 | 3.080 | 0.116 | 99.917 |
| Full base formulation with Cremophor ® RH40 (Table 11) | 4000 | 3.000 | 4.123 | 0.066 | 99.992 |
| Full base formulation with Polysorbate 20 (Table 11) | 4000 | 3.000 | 4.123 | 0.066 | 99.992 |
| Baseline | NA | 7.123 |  |  |  |

TABLE 14

Compositions of full base formulations with
Polysorbate 20 and Cremphor ® RH40

| Full Base Formulation | With Cremphor ® RH40 | With Polysorbate 20 |
|---|---|---|
| USP Purified Water or equivalent | qs 100% | qs 100% |
| Glycerin, USP | 1.50% | 1.50% |
| 1,3-propanediol, USP | 1.50% | 1.50% |
| Dimethicone | 0.05% | 0.05% |
| Polysorbate 20, USP | 0.00% | 0.50% |
| Cremophor ® RH40 | 0.50% | 0.00% |
| Nonoxynol-9, USP | 0.05% | 0.05% |
| pH 6 Buffer salt: Monobasic Potassium Phosphate, NF | 0.618% | 0.618% |
| pH 6 Buffer salt: Dibasic Sodium Phosphate, USP | 0.065% | 0.065% |

Although 0.5% Cremophor® RH40 appeared to be slightly less inhibitory than 0.5% polysorbate 20, both agents required 500 PPM of octenidine dihydrochloride to deliver >3 log reduction in viable count within 30 seconds of contact time.

The above data indicates that nonionic surfactants reduce the efficacy of octenidine dihydrochloride in a concentration dependent manner and concentration of surfactants and octenidine dihydrochloride can be balanced to provide desired efficacy of the formulated products. For example, polysorbate 20 (0.5% to 1.5%) may have >500 PPM of octenidine dihydrochloride to deliver rapid microbicidal efficacy.

Squeezing Volume

The squeezing volume of a wipe is a measure of the amount of antiseptic solution squeezed out from a soaked wipe. Wipes with high squeezing volumes tend to deliver more volume when scrubbing is performed. It has been found that the use of a bis-(dihydropyridinyl)-decane derivative (e.g., octenidine dihydrochloride) solution soaked into a polyester wipe may lower the squeezing volume, creating a undesirable feeling of dryness on the wipe. It has been found that by increasing the surfactant concentration in the solution, the squeezing volume of the wipe may be increased. Furthermore, it has been unexpectedly found that unlike biguanides (e.g., chlorhexidine gluconate), the addition of a bis-(dihydropyridinyl)-decane derivative (e.g., octenidine dihydrochloride) and heat treatment significantly changes the wetness feeling of the wipe and less solution can be squeezed out from the wipe.

The squeezing volume has been evaluated on different wipes with different formulations. The following formulations were prepared (in all of the below formulations the components are reported in terms of w/v basis, which can be calculated from a v/v basis when the final density of the formulation was determined):

Formulation 1 (F1)—0.4% w/v chlorhexidine digluconate and the remainder water.

Formulation 2 (F2)—0.4% w/v chlorhexidine digluconate, 1.5% w/v glycerin, 1.5% w/v 1,3-propanediol, 0.5% w/v Dow Corning 365 35% Dimethicone NF Emulsion, 1.5% w/v polysorbate 20, and the remainder water.

Formulation 3 (F3)—pure water.

Formulation 4 (F4)—0.4% w/v octenidine dihydrochloride and the remainder water.

Formulation 5 (F5)—0.5% w/v Dow Corning 365 35% Dimethicone NF Emulsion and the remainder water.

Formulation 6 (F6)—0.4% w/v octenidine dihydrochloride, 0.5% w/v Dow Corning 365 35% Dimethicone NF Emulsion, and the remainder water.

Formulation 7 (F7)—2.0% w/v glycerin, 2.0% w/v 1,3-propanediol, 0.5% w/v Dow Corning 365 35% Dimethicone NF Emulsion, 0.5% w/v polysorbate 20, and the remainder water.

Formulation 8 (F8)—0.4% w/v octenidine dihydrochloride, 2.0% w/v glycerin, 2.0% w/v 1,3-propanediol, 0.5% w/v Dow Corning 365 35% Dimethicone NF Emulsion, 0.5% w/v polysorbate 20, and the remainder water.

Formulation 9 (F9)—2.0% w/v glycerin, 2.0% w/v 1,3-propanediol, 1.0% w/v Dow Corning 365 35% Dimethicone NF Emulsion, 1.0% w/v polysorbate 20, and the remainder water.

Formulation 10 (F10)—0.4% w/v octenidine dihydrochloride, 2.0% w/v glycerin, 2.0% w/v 1,3-propanediol, 1.0% w/v Dow Corning 365 35% Dimethicone NF Emulsion, 1.0% w/v polysorbate 20, and the remainder water.

Formulation 11 (F11)—1.5% w/v glycerin, 1.5% w/v 1,3-propanediol, 0.57% w/v Dow Corning 365 35% Dimethicone NF Emulsion, 1.5% w/v polysorbate 20, and the remainder water.

Formulation 12 (F12)—0.4% w/v octenidine dihydrochloride, 1.5% w/v glycerin, 1.5% w/v 1,3-propanediol, 0.57% w/v Dow Corning 365 35% Dimethicone NF Emulsion, 1.5% w/v polysorbate 20, and the remainder water.

Formulation 13 (F13)—1.0% w/v glycerin, 1.50% w/v 1,3-propanediol, 0.14% w/v Dow Corning 365 35% Dimethicone NF Emulsion, 2.0% w/v polysorbate 20, and the remainder water.

Formulation 14 (F14)—0.4% w/v octenidine dihydrochloride, 1.0% w/v glycerin, 1.50% w/v 1,3-propanediol, 0.14% w/v Dow Corning 365 35% Dimethicone NF Emulsion, 2.0% w/v polysorbate 20, and the remainder water.

25 mL of each of Formulations 1-14 were individually applied to a different sample of the wipe of Example 8, i.e., producing 14 wipes each soaked with one of the formulations. Each of the soaked wipes was squeezed until no more solution was observed to come out of the wipe. The mass of each wipe was recorded before and after squeezing to obtain the squeezing volume, the results of which are reported below in Table 15.

TABLE 15

Squeeze Volumes

| Soaked Formulation | Squeeze Volume (g) |
| --- | --- |
| F1 (no OCT present) | 7.9 ± 1.2 |
| F2 (no OCT present) | 17 ± 1.4 |
| F3 (no OCT present) | 14 ± 2.7 |
| F4 (OCT present) | 3.2 ± 1.3 |
| F5 (no OCT present) | 15.4 ± 0.9 |
| F6 (OCT present) | 4 ± 1 |
| F7 (no OCT present) | 14.3 ± 1.5 |
| F8 (OCT present) | 5.7 ± 0.8 |
| F9 (no OCT present) | 16.5 ± 1.3 |
| F10 (OCT present) | 8.8 ± 1.6 |
| F11 (no OCT present) | 19.1 ± 1.1 |
| F12 (OCT present) | 16.2 ± 0.3 |
| F13 (no OCT present) | 18.5 ± 1.1 |
| F14 (OCT present) | 16.2 ± 1.6 |

Table 15 shows that the addition of octenidine dihydrochloride or chlorhexidine digluconate to water significantly lowered the squeeze volume delivered as compared to similar formulations lacking octenidine dihydrochloride and chlorhexidine digluconate. However, by increasing concentration of surfactant polysorbate 20, the difference between squeezing volume delivered by the wet wipes with and without octenidine dihydrochloride is reduced. Wipes loaded with 2% polysorbate 20 (F14) or 1.5% polysorbate 20 (F12) and 0.4% octenidine dihydrochloride delivered no significant volume difference from wet wipes loaded with 1.5% polysorbate 20 and 0.4% chlorhexidine digluconate (F2).

The effect of heat sterilization on the squeezing volume of moistened wipes has further been evaluated. The following formulations were prepared:

Formula 15 (F15)—0.4% w/v Octenidine dihydrochloride, 1.5% w/v Glycerin USP, 1.5% w/v 1,3 propanediol USP, 0.71% w/v Dow Corning 365 35% Dimethicone NF Emulsion, 1.0% w/v Kolliphor™ RH 40 (Polyoxyl 40 hydrogenated castor oil), 0.125% w/v noxynol 9 USP, 0.62% w/v monobasic potassium phosphate ($KH_2PO_4$), 0.06% w/v and dibasic sodium phosphate ($Na_2HPO_4$), and the remainder water.

Formula 16 (F16)—0.4% w/v Octenidine dihydrochloride, 1.5% w/v Glycerin USP, 1.5% w/v 1,3 propanediol USP, 0.14% w/v Dow Corning 365 35% Dimethicone NF Emulsion, 0.5% w/v Kolliphor™ RH 40 (polyoxyl 40 hydrogenated castor oil), 0.06% w/v noxynol 9 USP, 0.62% w/v monobasic potassium phosphate ($KH_2PO_4$), 0.06% w/v dibasic sodium phosphate ($Na_2HPO_4$), and the remainder water.

8 inch by 8 inch wipes of Examples 1, 3, 7, 8, 11, and 12 were each moistened with 25 mL of Formulations 15 and 16. Each wipe was placed into a borosilicate 500 mL media bottle, capped tightly, and autoclaved in a Getinge steam sterilizer with liquid cycle at 121° C. for 30 min. Upon completion of the cycle, the bottle was cooled down to room temperature before handling. Each wipe was folded to ¹⁄₁₂ of its original size and fixed with a rubber band. The wipe was set in a mold with the upper mold box containing the wipe and lower mold box holding the squeezed-out liquid. A 500 lbf loading force was applied on the folded wipe with a compression speed of 2 inches/min and held for 10 seconds before releasing. All the liquid squeezed out was collected in the lower box and disposed of after every squeezing application. The mass of each wipe was recorded before and after squeezing. The results are reported in Table 16 below.

TABLE 16

Squeeze Volumes pre/post Sterilization

| Wipe Example No. | 1 | 11 | 12 | 7 | 3 | 8 |
| --- | --- | --- | --- | --- | --- | --- |
| pre-sterilization (F16) | 17.8 | 16.65 | 16.72 | 16.44 | 17.55 | 16.94 |
| pre-sterilization (F15) | 16.11 | 15.54 | 16.5 | 16.06 | 17.48 | 15.59 |
| post-sterilization (F16) | 5.04 | 7.015 | 6.85 | 7.555 | 8.28 | 3.71 |
| post-sterilization (F15) | 11.98 | 12.955 | 13.805 | 10.57 | 11.55 | 7.23 |

All reported values are grams of liquid (original soaked weight minus final weight after squeezing).

The squeezing volume in Table 16 is provided for the wipes of Examples 1, 3, 7, 8, 11, and 12, moistened with either 0.5% Kolliphor™ RH 40 (F16) or 1% Kolliphor™ RH 40 (F15) under pre-and post-heat treatment conditions. Formulation 15 has higher surfactant concentration with 1% Kolliphor™ RH 40 and 0.125% Nonoxynol-9 than Formulation 16, which has 0.5% Kolliphor™ RH 40 and 0.06% Nonoxynol-9. Prior to heat treatment, there is no significant difference in squeezing volume between the wipes of Examples 1, 3, 7, 8, 11, and 12. There was also no significant difference between formulations F15 and 16; however, heat treatment within the autoclave shrinks the polyester wipe by about 1.5-3%. Without being bound by theory, it is believed that shrinkage after heat treatment lowered the average pore size of the wipe, thus increased the capillary pressure (capillary pressure is the force necessary to squeeze a droplet through a pore and is higher for smaller pore diameter) of the solution spread in the wipe, leading to a lowered squeezing volume for the wipes under compression. Post-autoclave treatment, wipes moistened with higher surfactant (F15) delivered a much higher squeezing volume than wipes with formulation F16 and the wipes of Examples 1, 3, 7, 8, 11, and 12 delivered a significantly lower squeezing volume than all other wipe materials. Changing wipe density, fiber length or fiber denier to increase or decrease the average pore size of the wipe is a possible approach to adjust the squeezing volume of the wipe. Based on these results, longer fibers, larger fiber denier and higher fiber density appear to result in a wipe with smaller pore size, which in turn leads to a larger formulation holding volume for the wipe and a lower squeezing volume. Increasing the surfactant concentration will also help with wetting the wipes. The same characteristics are found following heat treatment in that the squeezing volume is increased with greater surfactant concentration.

Additional data samples were collected in which the Kolliphor™ RH 40 in Formulations 15 and 16 was replaced with the same amount of polysorbate 20 (i.e., 1.0% w/v polysorbate 20 and 0.5% w/v polysorbate 20, respectively). These solutions were soaked into the wipe of Example 3. The pre and post sterilizing squeeze volumes were measured in the same manner as described above. It was found that the heat treatment also significantly lowered squeeze volume, and that increasing the polysorbate 20 content improved the squeezing volume. The squeeze volume pre- and post-heat treated, reduced from 18.50 grams to 4.64 grams when the polysorbate 20 concentration was 0.5% w/v. The squeeze volume pre- and post-heat treated, reduced from 18.50 grams to 9.43 grams when the polysorbate 20 concentration was 1.0% w/v. Thus, increasing the surfactant concentration to 1.0% allowed for a higher squeeze volume (18.50 grams to 9.43 grams).

While aspects of the present invention have been described in connection with illustrative implementations, it will be understood by those skilled in the art that variations and modifications of the aspects described above may be made without departing from the scope hereof. Other variations will be apparent to those skilled in the art from a consideration of the specification or from a practice along the lines as disclosed herein.

The invention claimed is:

1. An antiseptic formulation comprising:
    from about 0.2% w/v to about 1.0% w/v of an antiseptic agent comprising octenidine dihydrochloride;
    from about 0.1% w/v to about 5.0% w/v of a first skin conditioner comprising glycerin;
    from about 0.1% w/v to about 3.0% w/v of a second skin conditioner comprising 1,3-propanediol,
    from about 0.05% w/v to about 2.0% w/v of an antifoaming agent comprising dimethicone;
    from about 0.1% w/v to about 5.0% w/v of a first surfactant comprising polyoxyl 40 hydrogenated castor oil;
    from about 0.01% w/v to about 0.2% w/v of a second surfactant comprising nonoxynol-9;
    a first buffer salt comprising monobasic potassium phosphate;
    a second buffer salt comprising dibasic sodium phosphate; and
    water.

2. The antiseptic formulation according to claim 1, wherein the antiseptic agent is comprised in an amount from about 0.3% w/v to about 0.6% w/v.

3. The antiseptic formulation according to claim 1, wherein the first skin conditioner is comprised in an amount from about 0.1% w/v to about 3.0% w/v.

4. The antiseptic formulation according to claim 1, wherein the second skin conditioner is comprised in an amount from about 1.0% w/v to about 2.0% w/v.

5. The antiseptic formulation according to claim 1, wherein the antifoaming agent is comprised in an amount from about 0.1% w/v to about 1.0% w/v.

6. The antiseptic formulation according to claim 1, wherein the antifoaming agent is an emulsion containing 35% dimethicone.

7. The antiseptic formulation according to claim 1, wherein the first surfactant is comprised in an amount from about 0.5% w/v to about 3.0% w/v.

8. The antiseptic formulation according to claim 1, wherein the second surfactant is comprised in an amount from about 0.05% w/v to about 0.125% w/v.

9. The antiseptic formulation according to claim 1, wherein the first buffer salt is comprised in an amount of about 0.62% w/v.

10. The antiseptic formulation according to claim 1, wherein the second buffer salt is comprised in an amount of about 0.06% w/v.

11. A wipe comprising the antiseptic formulation according to claim 1.

12. The wipe according to claim 11 comprising a first fiber having a first denier and a second fiber having a second denier, wherein the first denier is different from the second denier.

13. The wipe according to claim 12 further comprising a third fiber having a third denier, wherein the third denier is different from the first denier and the second denier.

14. A package containing the wipe of claim 11, wherein the package comprises a metal foil or a metalized plastic.

15. An antiseptic formulation comprising:
    about 0.4% w/v of an antiseptic agent comprising octenidine dihydrochloride;
    about 1.5% w/v of a first skin conditioner comprising glycerin;
    about 1.5% w/v of a second skin conditioner comprising 1,3-propanediol,
    about 0.71% w/v of an antifoaming agent comprising an emulsion containing 35% dimethicone;
    about 1.0% w/v of a first surfactant comprising polyoxyl 40 hydrogenated castor oil;
    about 0.125% w/v of a second surfactant comprising nonoxynol-9;
    about 0.62% w/v of a first buffer salt comprising monobasic potassium phosphate;
    about 0.06% w/v of a second buffer salt comprising dibasic sodium phosphate; and
    water.

16. A wipe comprising the antiseptic formulation according to claim 15.

17. The wipe according to claim 16 comprising a first fiber having a first denier and a second fiber having a second denier, wherein the first denier is different from the second denier.

18. The wipe according to claim 17 further comprising a third fiber having a third denier, wherein the third denier is different from the first denier and the second denier.

19. A package containing the wipe of claim 16, wherein the package comprises a metal foil or a metalized plastic.

* * * * *